United States Patent [19]
Rosenberg

[11] Patent Number: 4,790,304
[45] Date of Patent: Dec. 13, 1988

[54] SELF-LOCKING PIN DEVICE PARTICULARLY USEFUL FOR INTERNALLY FIXING BONE FRACTURES

[76] Inventor: Lior Rosenberg, 13 Harduf Street, Omer, Beer Sheva, Israel

[21] Appl. No.: 690,323

[22] Filed: Jan. 10, 1985

[30] Foreign Application Priority Data

Jan. 20, 1984 [IL] Israel ............................................ 70736

[51] Int. Cl.⁴ .............................................. A61F 5/04
[52] U.S. Cl. .................... 128/92 Y; 623/18; 128/92
[58] Field of Search ............ 128/92 BC, 92 R, 92 D; 623/18; 411/58; 403/297, 277, 248

[56] References Cited

U.S. PATENT DOCUMENTS

| | | | |
|---|---|---|---|
| 1,060,543 | 4/1913 | Evans | 403/297 |
| 3,208,450 | 9/1965 | Abelson | 128/92 BC |
| 3,312,139 | 4/1967 | Di Cristina | 403/297 |
| 3,438,686 | 4/1969 | Stone | 411/58 |
| 4,227,518 | 10/1980 | Aginsky | 128/92 BC |
| 4,262,665 | 4/1981 | Roalstad | 128/92 BC |
| 4,481,702 | 11/1984 | Mitchell | 403/297 |
| 4,483,335 | 11/1984 | Tornier | 128/92 BC |
| 4,522,202 | 6/1985 | Otte | 128/92 BC |
| 4,562,598 | 1/1986 | Kranz | 128/92 BC |
| 4,681,477 | 7/1987 | Fischer | 403/405.1 |

FOREIGN PATENT DOCUMENTS

| | | | |
|---|---|---|---|
| 471336 | 2/1929 | Fed. Rep. of Germany | 411/58 |
| 215363 | 9/1967 | Sweden | 411/58 |

Primary Examiner—Gene Mancene
Assistant Examiner—Wenceslao J. Contreras
Attorney, Agent, or Firm—Benjamin J. Barish

[57] ABSTRACT

A self-locking pin device comprises a pin formed with enlargement in the region of its distal end; a tube received over the pin and having a diameter smaller than the enlargement, the tube being axially split at both its distal and proximal ends; and a collar received between the proximal ends of the pin and tube such that moving either the pin or tube splays the distal end of the tube about its axial split, and moving either the collar or the tube splays the proximal end of the tube along its axial split.

22 Claims, 3 Drawing Sheets

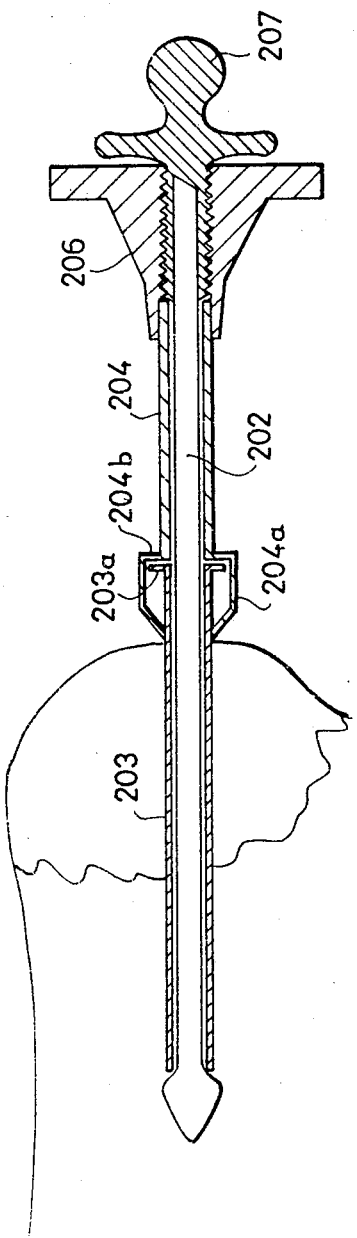
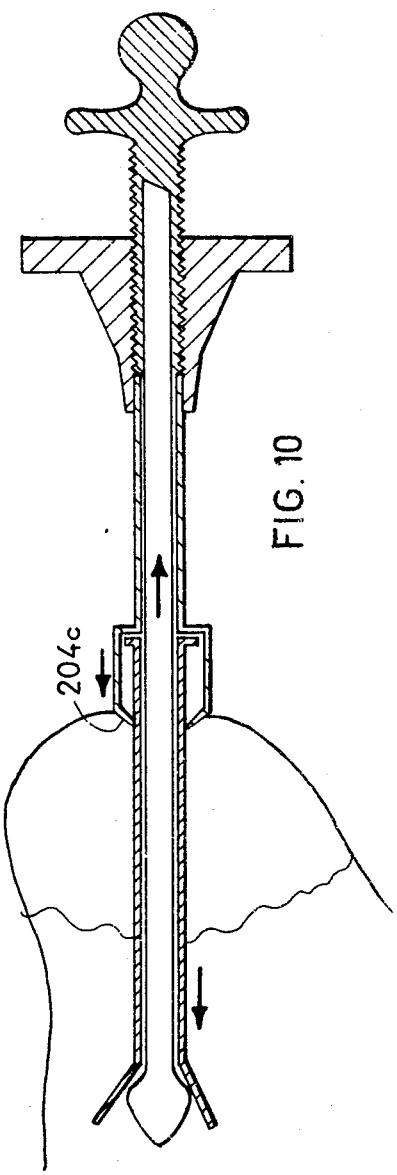
FIG. 9
FIG. 10

SELF-LOCKING PIN DEVICE PARTICULARLY USEFUL FOR INTERNALLY FIXING BONE FRACTURES

BACKGROUND OF THE INVENTION

The present invention relates to self-locking pin devices. The invention is particularly useful for internally fixing bone fractures, and is therefore described below with respect to this application, but it will be appreciated that the invention could advantageously be used in other applications as well.

Fractures of the phalanges (i.e., the bones in the fingers and toes) are one of the most common encountered in the human skeleton. Many of these fractures and those of other small bones, and small bone fragments, must be treated by internal fixation methods in order to achieve good anatomical position, early mobilization, and fast and complete rehabilitation of the injured patient. The internal fixation techniques commonly followed today use Kirschner wires (K-wires), intermeduallary pins, wirings, plates, or screws, and combinations of the foregoing, the object being to reach the best anatomical and functional condition of the traumatized bone in the simplest operative procedure and with a minimal use of foreign implanted stabilizing material.

A fixation of the fractured line by a single K-wire is usually the least harmful and the easiest to execute. However, a single K-wire stabilizes only a single spacial plane of movement, whereas the forces acting on the fractured bone are usually in more than one plane; therefore this technique is impractical in most cases. Probably the most common procedure is to use two crossed K-wires transcutaneously or through an explorative incision, but this is a rather extensive procedure and produces a relatively large mass of foreign implanted material. Other internal fixation methods involve even more extensive procedures, with a greater iatrogenic trauma to the injury, and with a larger mass of foreign implanted material, in order to produce a three-place stabilization of the fractured bone.

SUMMARY OF THE INVENTION

An object of the present invention is to provide a self-locking pin device particularly useful for internally fixing bone fractures and having advantages in the above respects over the presently used techniques. Another object of the invention is to provide a self-locking pin device which may be used in other applications, wherever a firm fixation is required with respect to multiplanar forces, and access is provided only from one side of the object to be fixed.

According to a broad aspect of the present invention, there is provided a self-locking pin device comprising: a pin having proximal and distal ends and formed with an enlargement in the region of its distal end; a tube received over the pin and having a diameter smaller than said enlargement, the tube being axially split at both its distal and proximal ends; and a collar received between the proximal ends of the pin and tube, such that effecting relative axial movement between the enlargement at the distal end of the pin and the distal end of the tube splays outwardly the distal end of the tube about its axial split, and effecting relative axial movement between the collar and the proximal end of the tube splays outwardly the proximal end of the tube along its axial split.

According to a further feature in one of the preferred embodiments of theinvention described below, the device further includes manually-gripping means attachable to the proximal end of the pin, tube, and collar, to facilitate their insertion and the splaying of the two ends of the tube. More particularly, the manually-gripping means comprises: a sleeve formed with an axial bore for receiving the proximal end of the pin, and with an annular recess extending axially of its distal end for receiving the proximal end of the tube; and a locking ring movable either to a locking position at the distal end of the sleeve, wherein it cams same inwardly to cause it to grip the pin and tube, or to a releasing position away from the distal end of the sleeve causing it to release the pin and tube.

As will be described below, self-locking pin devices constructed in accordance with the foregoing features may be used for internally fixing fractures in an operative procedure which is simple, less traumatic than presently followed procedures, involves a minimal use of foreign implanted material, and stabilizes the fracture line in three spacial planes.

Further features and advantages of the invention will be apparent from the description below.

BRIEF DESCRIPTION OF THE DRAWINGS

The invention is herein described, by way of example only, with reference to the accompanying drawings, wherein:

FIGS. 7 and 8 illustrate a still further form of self-locking pin device constructed in accordance with the present invention, the device being equipped with manually-gripping means for facilitating the use of the device, FIG. 7 illustrating the components of the manually-gripping means in their locking positions, while FIG. 8 illustrates them in their releasing positions;

and FIGS. 9 and 10 illustrate a still further variation of the invention.

DESCRIPTION OF PREFERRED EMBODIMENTS

Figure 1:
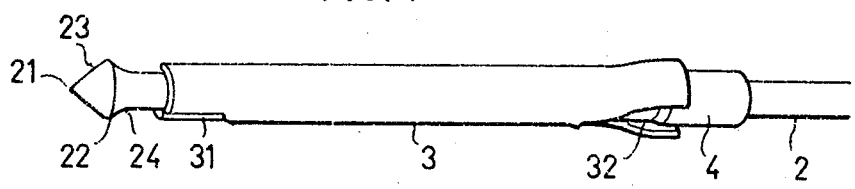
FIG. 1 is a three-dimensional view illustrating one form of self-locking pin constructed in accordance with the present invention, FIG. 1a illustrating a variation.

The self-locking pin device illustrated in FIGS. 1-5 is particularly useful for internally fixing bone fractures. It comprises three basic components, namely: a pin 2; a tube 3 received over pin 2; and a collar 4 received between one end, namely the proximal end, of pin 2 and tube 3.

Pin 2 may be conventional K-wire commonly used in internally fixing bone fractures. Such wires are made of stainless steel and generally are of diameters ranging from 0.5 to 3.0 mm. In this case, the distal end of pin 2 is formed with: a pointed tip 21, an enlargement 22 inwardly spaced from the pointed tip, a cutting edge 23 between tip 21 and enlargement 22, and a tapered junction 24 between enlargement 22 and the inner part of the pin.

Figure 1A:
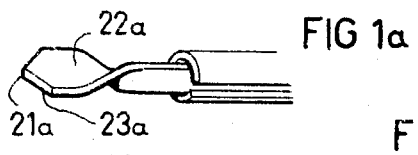

According to the variation illustrated in FIG. 1a, the enlargement, therein designated 22a, is formed by flattening end of pin 2 in order to widen it, and then giving it a twist. The opposite sides are formed with cutting edges 23a and with a pointed tip 21a as in FIG. 1.

The outer tube 3 may also be of stainless steel. It is received over pin 2, but its inner diameter is less than that of the in enlargement 22. The distal end of tube 3 is formed with two or more axially-extending slits 31; and the proximal end of the tube is similarly formed with two or more axially-extending slits 32. Slits 31 permit the distal end of the tube to be splayed, i.e. bent outwardly, as shown at 33 in FIGS. 3 and 4; and similarly, slits 32 permit the proximal end of the tube to be splayed as shown at 34.

Collar 4 received over the proximal end of pin 2 between it and the proximal end of tube 3, may also be made of stainless steel. It has the same inner and outer diameters as tube 3, but is of much shorter length, being in the order of about twice the length of the axial slits 32 formed in the proximal end of the tube. The distal end of collar 4 is preferably formed with a tapered leading edge, as shown at 41 in FIG. 3, to facilitate the insertion of the collar between pin 2 and tube 3, and its movement axially of the pin in order to splay the proximal end of the tube, as will be described more particularly below.

Figure 2:
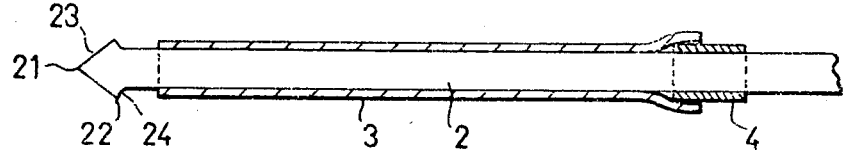
FIG. 2 is a side elevational view, partly in section, of the device of FIG. 1.
Figure 3:
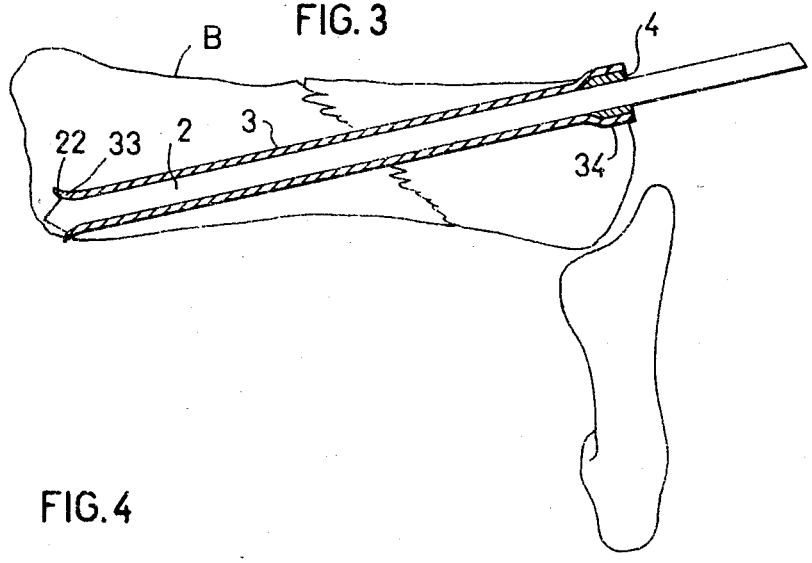
FIG. 3 illustrates the manner of using the device of FIGS. 1 and 2 for internally fixing a bone fracture.
Figure 4:
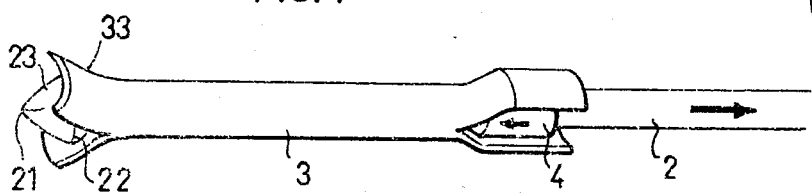
FIG. 4 is a view similar to that of FIG. 1, but showing the operations performed for fixing the device in the bone.
Figure 5:
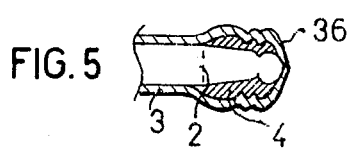
FIG. 5 is a fragmentary view illustrating the end of the device when the procedure has been completed.

The self-locking pin device illustrated in FIGS. 1 and 2 may be used in the following manner for internally fixing a fracture in a bone B as illustrated in FIG. 3.

Thus, the device, with its components assembled as illustrated in FIGS. 1 and 2, is introduced into the fractured bone B by rotating the device such that the pointed and cutting edge 23, at the distal end of pin 2, serves as a drill bit for penetrating the bone. Another alternative is to introduce the device in predrilled holes through the bone. After the device has been inserted into bone B to the position illustrated in FIG. 3, pin 2 is displaced in the outer direction as shown by arrow $A_1$ in FIG. 4, while collar 4 is displaced in the inner direction as shown by arrow $A_2$. Displacing pin 2 in the direction of arrow $A_1$ causes the enlargement 22 at the distal end of the pin to splay or bend outwardly the distal end of tube 3 along its axial split 31, a shown at 33 in FIGS. 3 and 4; and displacing collar 4 in the direction of arrow $A_2$, causes the proximal end of tube 3 to be bent outwardly of splayed as shown at 34 in FIGS. 3 and 4. Pin 2 is thus firmly fixed at both its ends within the fractured bone, thereby firmly stabilizing the fracture line in the three spacial planes.

The proximal end of pin 2 may be left protruding from bone and skin, for use in connecting the pin to an elastic bandage or to a fixation or treatment device, or for use latter in facilitating the extraction of the pin after the bone has healed. Alternatively, the proximal end of pin 2 can be severed, and the proximal end of tube 3 crimped over the proximal end of tube 2 and of collar 4, as shown at 36 in FIG. 5.

When removing the pin device, the reverse procedure is followed; that is, the crimped end 36 of tube 3 is opened; collar 4 is pulled in the outer direction (opposite to direction $A_2$ of FIG. 4); and pin 2 is pushed in the inner direction (i.e. opposite to direction $A_1$ in FIG. 4), whereupon the device is released from the bone and may be pulled outwardly therefrom.

Figure 6:
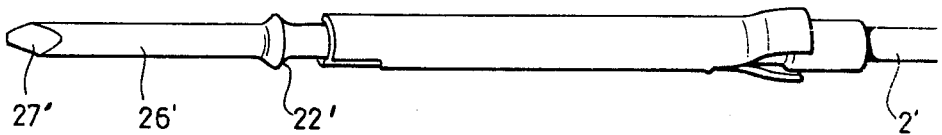
FIG. 6 is a three-dimensional view illustrating another form of self-locking pin device constructed in accordance with the present invention.

FIG. 6 illustrates a modification, wherein the distal end of the pin, therein designated 2', is formed with an extension for effecting external fixation or for better axial stabilization in larger bones. Thus, in this modification, the enlargement 22' is formed somewhat inwardly of the distal end of pin 2' to provide the extension 26'. The distal tip of the pin is here also pointed and formed with a sharpened edge, as shown at 27', to facilitate its introduction into the bone by rotation in the same manner as described above.

Figure 7:
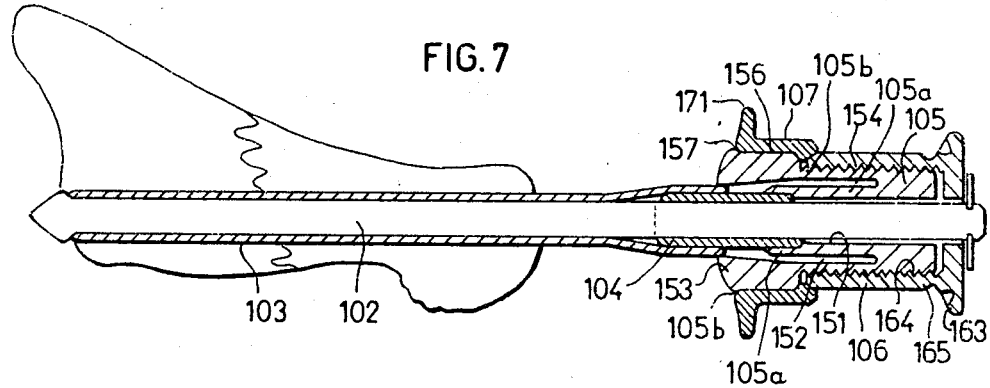
Figure 8:
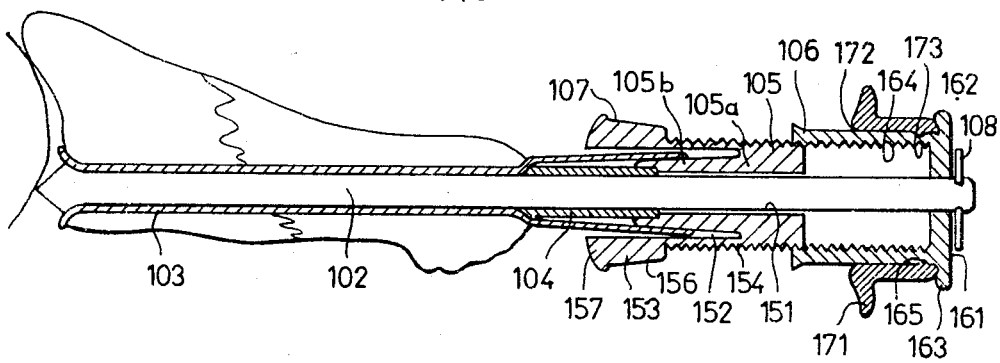

FIGS. 7 and 8 illustrate a further embodiment of the invention wherein the device is equipped with manually gripping means to facilitate the insertion of the pin and the splaying of the two ends of the tube when fixing the pin within the fractured bone. Thus, the device illustrated in FIGS. 7 and 8 also includes a pin 102 enclosed within a tube 103 and having a collar 104 between the distal ends of the pin and tube, all having the same structure as described above with respect to pin 2, tube 3, and collar 4, respectively. The device of FIGS. 7 and 8, however, includes additional components serving as the manually-gripping means, namely: a sleeve 105, a cap 106, a locking ring 107, and a retainer clip 108.

Sleeve 105 is formed with an axial bore 151 for receiving the proximal end of pin 102. Sleeve 105 is further formed with an annular recess 152 extending axially from its distal end for most of the length of the sleeve, to provide an inner sleeve section 105a and an outer sleeve section 105b, the latter terminating in a resilient extension 153 at the distal end of the sleeve. The outer sleeve section 105b is externally threaded, as shown at 154, from extension 153 to the proximal end of the sleeve. The distal resilient end 153 of the sleeve is formed with an outer tapered face 156, increasing in diameter towards the distal end of the sleeve, and terminating in an annular rib 157 at the distal end of the sleeve.

Cap 106 is formed with an end wall 161 having a central aperture 162 for receiving the proximal end of pin 102. Wall 161 is of larger diameter than the remainder of the cap to define an enlarged head, as shown at 163. Retainer clip 108 received on the proximal end of pin 102 retains the cap on the pin, but permits the cap to be rotated with respect to the pin. Cap 106 further includes internal threads 164 adapted to mate with external threads 154 in sleeve 105. In addition, cap 106 is formed with an annular recess 165 adjacent to its enlarged head 163.

Locking ring 107 has an internal diameter substantially equal to the outer diameter of cap 106 to permit the locking ring to be slid along the outer face of the cap, and then over the tapered face 156 of sleeve 105. An enlarged head 171 at the distal end of the locking ring facilitates sliding it. The locking ring is further formed with an outwardly tapered surface 172 engageable with the annular rib 157 in sleeve 105 when the locking ring is in its locking position (FIG. 7), and with an internal annular rib 173 receivable within annular recess 165 in cap 106 when the locking ring is in its released position (FIG. 8).

The self-locking pin device illustrated in FIGS. 7 and 8 may be used in the following manner:

Normally, the device would be assembled and supplied to the user in the condition illustrated in FIG. 7, wherein: pin 102 passes through sleeve 105 and cap 106; tube 103 is received within the annular recess 152 formed in sleeve 105; and collar 104 is received between pin 102 and tube 103 and bears, at its proximal end, against the end of the inner sleeve section 105a. In addition, in this assembled condition of the device, the locking ring 107 is in its locking position overlying extension 153 of the outer sleeve section 105b, limiting against annular rib 157. Because of the tapered surface 156 of the outer sleeve section 105b, the latter is cammed inwardly by the locking ring 107 to tightly grip tube 103 and collar 104 between it and pin 102. Cap 106, in this assembled condition of the device, is threaded to its innermost position bearing against the end of locking ring 107, and thereby firmly locks it in its locking condition.

The device may thus be introduced into the fractured bone by rotation, in the manner described above with respect to FIGS. 1-5, cap 106 providing a convenient manual grip for this purpose. As soon as the device has been introduced completely into the fractured bone, locking ring ring 107 is manually slid from its locking position against rib 157 on sleeve 105, to its unlocking position against head 163 of cap 106, and is retained in this unlocking position by its rib 173 received within annular recess 165 formed in the cap. This releases the gripping effected between tube 103, collar 104, and pin 102.

At this time, cap 106 may be rotated to unthread itself from threads 154 of sleeve 105, which thereby causes pin 102 to move outwardly, and the collar 104 to move inwardly (in the same directions as indicated by arrows $A_1$ and $A_2$, respectively, in FIG. 4) to thereby splay the opposite ends of tube 102 in the same manner as described above with respect to FIG. 4, thereby firmly fixing the device in the fractured bone.

After the device has been thus fixed in the fractured bone, the protruding portions of the pin 102 and tube 103 may be left protruding, with or without the manually-griping members 105-108, or may be severed and the ends crimped, as described above with respect to FIGS. 1-5.

The procedure for extracting the pin is substantially reversed to that described above for introducing it. Thus, when extracting the pin, the cap 106 is threaded inwardly over sleeve 154, and the protruding pin 102 is then pushed slightly inwardly by hand so as to release the inner end of the splayed end of tube 103. Locking collar 107 is then moved over the resilient extension 153 of sleeve 105 to lock the parts; and then pin 102 is withdrawn from the bone, this being facilitated by gripping cap 106.

In the modification illustrated in FIGS. 7 and 8, collar 104 is shown as a separate distinct member as in the embodiments illustrated in FIGS. 1-6. However, it will be appreciated that this collar could be integrally formed with the inner section 105a of sleeve 105 since it moves with it.

Another modification would be to have cap 106 fixedly connected to or integral with pin 102. In this case, the rotation of the cap would cause the pin also to turn in the same direction, and locking the cap by the locking ring will stabilize the pin as well.

A still further variation would be to omit the cap 106, and instead, to provide the proximal part of the pin with means for rotating it by the use of a tool, such as a screwdriver or wrench. In this variation, the movement of the collar could be guided by small protuberances formed on its outer face movable within the slits in the proximal end of the tube.

FIGS. 9 and 10 illustrate a still further variation, including a pin 202 enclosed within a tube 203 split at its distal end, and formed with an annular flange 203a at its proximal end. The latter flange is enclosed by an enlarged portion 204a of a sleeve 204, such that annular wall 204b of sleeve 204 bears against annular flange 203a of tube 203. The proximal end of sleeve 204 is fixed to a collar 206, and the proximal end of pin 202 is fixed to a cap 207 threadedly received within collar 206. Thus, when cap 207 is threaded outwardly from collar 206, to the position illustrated in FIG. 10, annular wall 204b of sleeve 204 engages annular flange 203a of tube 203, pushing the tube in the inward direction and pulling the pin in the outward direction, as shown in FIG. 10, thereby firmly anchoring the pin between the split ends of tube 203 and annular wall 204c of sleeve 204.

While the invention has been described with respect to several embodiments, particularly applicable to internally fixing bone fractures, it will be appreciated that the described devices could be used in many other applications, for firmly anchoring a self-locking pin to a body, where there is access only from one side of the body, for example, for mounting a self-locking pin through a wooden, metal, or concrete panel wherein the pin is to be fixed to the opposite sides of the panel but access is provided from only one side of the panel.

Many other variations, modifications, and applications of the invention will be apparent.

What is claimed is:

1. A self-locking pin device comprising:
    a pin having proximal and distal ends and formed with an enlargement in the region of its distal end;
    a tube received over said pin and having a diameter smaller than said enlargement, said tube being axially split at both its distal and proximal ends;
    a collar received between the proximal ends of said pin and tube, such that affecting relative axial movement between the enlargement at the distal end of the pin and the distal end of the tube splays outwardly the distal end of the tube about its axial split, and effecting relative axial movement between the collar and the proximal end of the tube splays outwardly the proximal end of the tube along its axial split;
    and manually gripping means attachable to the proximal end of the pin, tube and collar, to facilitate their insertion and the splaying of the two ends of the tube.

2. The device according to claim 1, wherein said distal end of a pin is formed with a cutting edge to facilitate inserting the pin by rotation.

3. The device according to claim 1, wherein the distal edge of the collar is tapered.

4. The device according to claim 1, wherein said enlargement is formed at the distal end of the pin.

5. The device according to claim 1, wherein said pin is of a diameter of 0.5 to 1.5 mm.

6. The device according to claim 1, wherein said pin is of stainles steel.

7. The device according to claim 6, wherein said tube and collar are also of stainless steel.

8. The device according to claim 1, wherein said manually gripping means comprises:
    a sleeve formed with an axial bore for receiving the proximal end of the pin, and with an annular recess extending axially of its distal end for receiving the proximal end of the tube;
    and a locking ring movable either to a locking position at the distal end of said sleeeve, wherein it cams same inwardly to cause it to grip said pin and tube, or to a releasing position away from said distal end of the sleeve causing same to release said pin and tube.

9. The device according to claim 8, wherein the distal end of said sleeve is formed with a tapered outer face increasing in diameter towards its distal end, which tapered outer face receives said locking ring when moved to its locking position.

10. The device according to claim 9, wherein said tapered outer face of the sleeve terminates in an annular rib at its distal end, which rib serves as a limit for the locking ring when moved to its locking position.

11. The device according to claim 8,
wherein said manually gripping means further comprises: a cap received over the proximal end of the sleeve and retaining said locking means in its locking position over the distal end of said sleeve.

12. The device according to claim 11, wherein the proximal end of said sleeve is formed with external thread mating with internal threads formed in said cap.

13. The device according to claim 12, wherein said cap is formed with a central bore receiving the proximal end of said pin.

14. The device according to claim 13, wherein the proximal end of said pin passes through said central bore of the cap, the device further including: a retainer clip for retaining the cap on the proximal end of the pin while permitting the cap to be rotated with respect to the pin.

15. The device according to claim 13,
wherein said cap is formed at its proximal end with an enlarged head serving as a limit for the locking ring when moved to its releasing position.

16. The device according to claim 15, wherein said cap is further formed at its proximal end with an annular recess for receiving an annular rib formed on the inner face of said locking ring for retaining same in its releasing position.

17. The device according to claim 8,
wherein said collar is formed as a separate member from, and engageable with, said sleeve.

18. The device according to claim 8,
wherein said collar is integrally formed with said sleeve.

19. The device according to claim 8,
wherein said cap is formed as a separate member from said pin.

20. The device according to claim 8,
wherein said cap is fixedly connected to the proximal end of said pin.

21. The device according to claim 8,
wherein the proximal end of said pin is formed with means for rotating same, and said collar includes protuberances formed on its outer face movable within the slits in the proximal end of said tube.

22. A self-locking pin device comprising:
a pin having proximal and distal ends and formed with an enlargement in the region of its distal end;
a tube received over said pin and having a diameter smaller than said enlargement, said tube being axially split at both its distal and proximal ends;
and a collar received between the proximal ends of said pin and tube, such that effecting relative axial movement between the enlargement at the distal end of the pin and the distal end of the tube splays outwardly the distal end of the tube about its axial split, and effecting relative axial movement between the collar and the proximal end of the tube splays outwardly the proximal end of the tube along its axial split;
said enlargement being formed inwardly of the distal end of the pin to provide an extension for effecting external fixation to the pin.

* * * * *